United States Patent
Lee et al.

(10) Patent No.: US 6,469,113 B1
(45) Date of Patent: Oct. 22, 2002

(54) METHOD FOR PRODUCING SUPPORTED METALLOCENE CATALYST AND OLEFIN POLYMERIZATION PROCESS USING THE SAME

(75) Inventors: Bun-Yeoul Lee; Jae-Seung Oh, both of Taejeon (KR)

(73) Assignee: LG Chemical Ltd., Seoul (KR)

( * ) Notice: Subject to any disclaimer, the term of this patent is extended or adjusted under 35 U.S.C. 154(b) by 0 days.

(21) Appl. No.: 09/445,647

(22) PCT Filed: Apr. 9, 1999

(86) PCT No.: PCT/KR99/00169

§ 371 (c)(1),
(2), (4) Date: Dec. 9, 1999

(87) PCT Pub. No.: WO99/52949

PCT Pub. Date: Oct. 21, 1999

(30) Foreign Application Priority Data

Apr. 9, 1998 (KR) ............................................. 98-12660

(51) Int. Cl.[7] .......................... C08F 4/656; C08F 4/655
(52) U.S. Cl. .................... 526/126; 526/129; 526/160; 526/945; 502/120; 502/158; 502/152
(58) Field of Search ................................. 526/126, 129, 526/943, 160; 502/120, 158, 152

(56) References Cited

U.S. PATENT DOCUMENTS

| | | | |
|---|---|---|---|
| 3,670,043 A | 6/1972 | Kubicek et al. ............. 260/683 |
| 3,939,213 A | 2/1976 | Homeier et al. ............. 260/615 |
| 3,957,697 A | 5/1976 | Schlatzer ........................ 260/2 |
| 4,197,419 A | 4/1980 | Schrock ........................ 585/511 |
| 4,892,851 A | 1/1990 | Ewen et al. ................. 502/104 |
| 5,001,221 A | 3/1991 | Van Broekhoven ......... 528/392 |
| 5,017,714 A | 5/1991 | Welborn, Jr. .................. 556/12 |
| 5,026,798 A | 6/1991 | Canich ........................ 526/127 |
| 5,036,034 A | 7/1991 | Ewen .......................... 502/117 |
| 5,057,475 A | 10/1991 | Canich et al. .............. 502/104 |
| 5,096,867 A | 3/1992 | Canich ........................ 502/103 |
| 5,120,867 A | 6/1992 | Welborn, Jr. .................. 556/12 |
| 5,126,301 A | 6/1992 | Tsutsui et al. .............. 502/108 |
| 5,145,819 A | 9/1992 | Winter et al. ............... 502/117 |
| 5,202,398 A * | 4/1993 | Antberg et al. ............. 526/129 |
| 5,225,501 A | 7/1993 | Fujita et al. ................. 526/127 |
| 5,234,878 A | 8/1993 | Tsutsui et al. .............. 502/103 |
| 5,266,544 A | 11/1993 | Tsutsui et al. .............. 502/113 |
| 5,466,766 A | 11/1995 | Patsidis et al. ............. 526/129 |
| 5,580,939 A | 12/1996 | Ewen et al. ................. 526/127 |
| 5,633,394 A | 5/1997 | Welborn, Jr. et al. ......... 556/11 |
| 5,658,982 A | 8/1997 | Baardman et al. .......... 524/711 |
| 5,814,574 A | 9/1998 | McNally ..................... 502/103 |
| 5,824,620 A * | 10/1998 | Vega et al. .................. 502/117 |
| 6,143,685 A * | 11/2000 | Llinas et al. ................ 502/152 |

FOREIGN PATENT DOCUMENTS

EP 0 293 815 A1 12/1999

* cited by examiner

Primary Examiner—David W. Wu
Assistant Examiner—Caixia Lu
(74) Attorney, Agent, or Firm—Knobbe, Martens, Olson and Bear LLP

(57) ABSTRACT

The present invention relates to a method for producing supported metallocene catalyst and an olefin polymerization process using same, and more particularly to a method for manufacturing supported metallocene catalyst by reacting metallocene catalyst having an alkoxysilane group at a part of a ligand with a support having a highly reactive siloxane group at the surface, and the olefin polymerization process using the same.

14 Claims, 1 Drawing Sheet

METHOD FOR PRODUCING SUPPORTED METALLOCENE CATALYST AND OLEFIN POLYMERIZATION PROCESS USING THE SAME

CROSS REFERENCE TO RELATED APPLICATION

This application is based on application No 98-12660 filed in the Korean Industrial Property Office on Apr. 9, 1998, the content of which is incorporated hereinto by reference.

BACKGROUND OF THE INVENTION (a) Field of the Invention

The present invention relates to a method for producing supported metallocene catalyst and an olefin polymerization process using same, and more particularly to a method for manufacturing supported metallocene catalyst by reacting metallocene catalyst having a hydrocarboxy silane group at a part of a ligand with a support having a highly reactive siloxane group at the surface, and the olefin polymerization process using the same.

(b) Description of the Related Art

In 1976, Professor Kaminsky of Germany reported that olefin polymerization could be made by using MAO (methylaluminoxane) compound obtained through partial hydrolysis of trimethylaluminum as a cocatalyst and by zirconocendichlodide compound as a catalyst (A. Anderson, J. G. Corde. J. Herwing, W. Kaminsky, A. Merk, R. Mottweiler, J. Pein, H. Sinn, and Vollmer, Angew. Chem, Int, Ed. Engl., 15, 630, 1976). This homogeneous catalyst shows unique polymerization characteristics that conventional Ziggler-Natta catalysts can not embody. That is, molecular weight distribution of the produced polymer is narrow, copolymerization is easy, and the second monomer distribution is uniform. Not only molecular weight or the degree of copolymerization can be changed freely by simply changing the catalyst ligand structure, but also tacticity of polymer can be controlled according to the molecular symmetry of catalyst. These unique characteristics not only opened up a way of new polymers not obtainable through conventional Ziggler-Natta catalyst, but also the way of tailor-maid polymers. Accordingly, studies on this catalyst have been actively going on.

Polyethylene manufacturing processes are can be classified into the high pressure process, the solution process, the slurry process, and the gas phase process. Efforts to replace only the catalysts of these processes with metallocene catalysts are being made. In the gas phase or slurry processes, particle morphology and bulk density of the produced polymer should be controlled to increase output per reactor unit capacity, and a reactor fouling should be solved for the continuous operation. In order to increase the bulk density and to solve the reactor fouling, supported catalyst should be used in those process. As a result of this, various efforts to support metallocene catalyst on suitable solid material have been made.

One of the supporting methods of the metallocene catalyst is to synthesize metallocene compounds having functional groups such as alkoxysilaone group on a part of a ligand and then to react these functional groups with hydroxyl group of the silica (R. Jackson, J. Ruddlesden., and D. J. Thompson, J. Organomet. Chem. 125 (1997), 57; B. L. Booth, G. C. Offumme, C. Stacey, and P. J. T. Tait, J. Organomet. Chem. 315 (1986), 145; European Patent No. 293815). In this case, using silica OH group according to such a reaction is plainly stated in the below reaction formula 1. European Patent No. 293815, page 5, lines 11 to 15 describe that support having an amount of hydroxyl group on its surface of 0.5 ~50 mmol/g, particularly 1~20 mmol/g, and more desirably 1.5~10 mmol/g, is used.

<Reaction Formula 1>

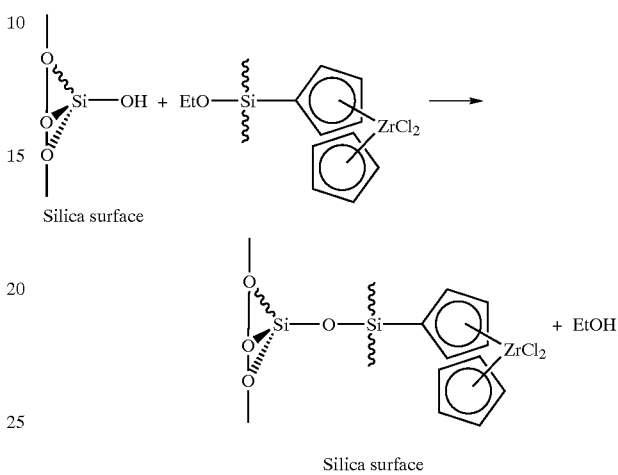

Silica surface

However, when the compounds are reacted with the hydroxy group of the surfaces, the following various side reactions can be accompanied (D. J. Cardin, M. F. Lappert, and C. L. Raston, Chemistry of Organo-Zirconium and Hafnium Compounds, John Wiley & Song 1986, 96 page).

<Reaction Formula 2>

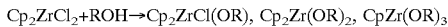

There is a sufficient possibility that this kind of reaction could also occur when the metallocene compounds are reacted with the silica having hydroxyl group. This kind of side reaction could cause process problems during the polymerization reaction as it could possibly be leached out, when it was activated with aluminoxane. The polymer may show different characteristics from the one obtained from non-supported catalyst, thus losing advantages obtainable by a supported catalyst system.

SUMMARY OF THE INVENTION

It is an object of the present invention to provide a method for manufacturing a supported metallocene catalyst by reacting metallocene compounds having an alkoxysilane group with highly reactive siloxane groups, which are produced when the supporting materials are dried at high temperature as in the reaction formula 4, not with OH groups of the supporting materials.

By using this method, supporting materials having much less amount of surface hydroxyl groups should be used in order to eliminate the various side reactions caused by hydroxyl groups.

Also in accordance with the present invention, there is provided a method of manufacturing a supported metallocene catalyst. The method includes the step of reacting a silica with using a metallocene catalyst having an alkoxysilane group. The silica has siloxane groups with high activity on the surface thereof by drying a silica at a temperature above 600° C.

Still further in accordance with the present invention there is provide a method of polymerizing olefinic monomer. The method includes the step of polymerizing olefinic monomers by using a supported metallocene catalyst and a cocatalyst. The supported metallocene catalyst is prepared by reacting a silica with a metallocene catalyst having an alkoxysilane group. The silica has siloxane groups with high activity on the surface thereof by drying a silica at a temperature above 600° C.

<Reaction Formula 4>

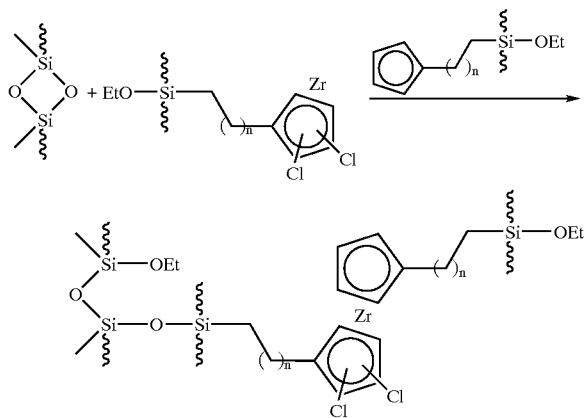

BRIEF DESCRIPTION OF THE DRAWINGS

A more complete appreciation of the invention, and many of the attendant advantages thereof, will be readily apparent as the same becomes better understood by reference to the following detailed description when considered in conjunction with the accompanying graph, wherein.

DETAILED DESCRIPTION OF THE INVENTION

Figure 1:
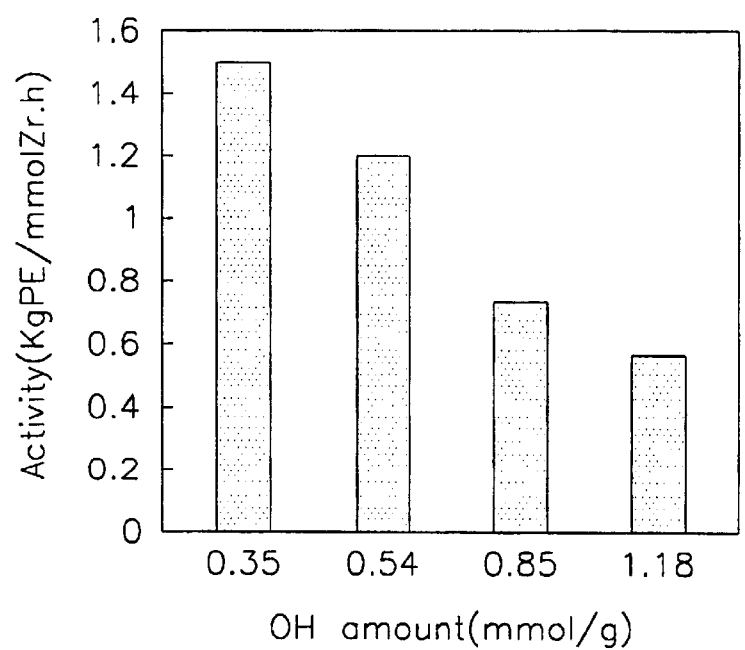
FIG. 1 is a graph showing the relation with hydroxyl group of silica surface and activity of catalyst.

The present invention relates to a supporting method decreasing various side reactions by using support having less surface OH groups. When silica is dried at a high temperature, surface hydroxyl groups are removed into water generating siloxane groups like the below reaction formula 3. It has been reported that with drying temperatures of 200~500° C., easily removable hydroxyl groups are reversibly removed to generate a low reactive siloxane group, but in case of drying temperatures over 600° C., hydroxyl groups are forcibly removed into water to generate a siloxane group, which has high ring strain and very high reactivity (I.-S. Chuang and G. E. Maciel, Journal of American Chemical Society, 1996, vol. 118, 401). Highly reactive siloxane groups, produced by drying at over 600° C., were reported to react with alkoxysilane group as the following reaction formula 3 (J. Blumel, Journal of American Chemical Society, 1995 vol. 117, 2112,; L. H. Dubois, Journal of American Chemical Society, 1993, vol. 115, 1190).

<Reaction Formula 3>

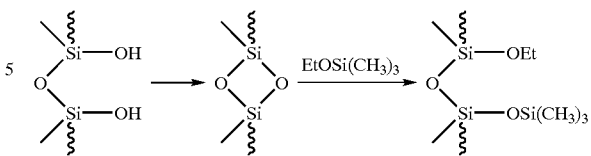

The present invention is characterized in supporting the metallocene compounds by reacting metallocene catalyst having alkoxysilane group with the highly reactive siloxane group of the supporting materials as shown in reaction formula 4, not with surface OH groups.

By using this method, supporting materials having much less amount of surface hydroxyl groups are used in order to eliminate the various side reactions caused by hydroxyl groups.

<Reaction Formula 4>

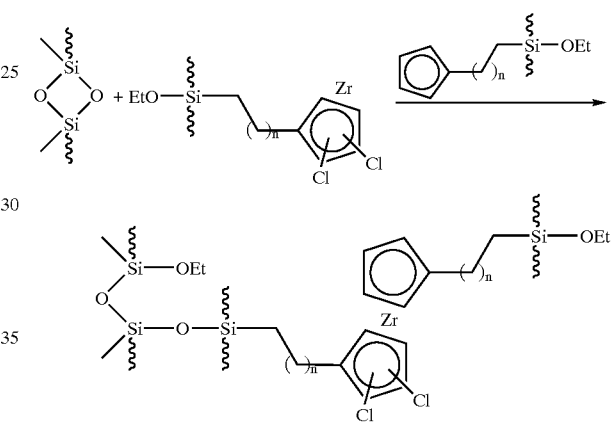

The present invention is described in detail as follows. Catalyst having alkoxysilane group, which is usable in the present invention, is generally as follows:

Compound, where at least more than one of hydrogen radicals among $R^3$, $R^4$ and B in the compounds depicted Formula 2 or 3, which show the activity for the olefin polymerization when activated with cocatlyst, were substituted with radical depicted below Formula 1.

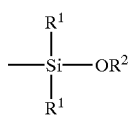  [Formula 1]

where $R^1$ is selected from the group consisting of a hydrogen radical, an alkyl radical, an arylalkyl radical, an alkylaryl radical, an aryl radical, of 1 to 20 carbon atoms, a halogen radical, and an alkoxy radical of 1 to 20 carbon atoms; and $R^2$ is selected from the group consisting of an alkyl radical, an arylalkyl radical, an alkylaryl radical, and an aryl radical, of 1 to 20 carbon atoms.

$$(C_5R^3{}_m)_pB_s(C_5R^3{}_m)MQ_{3-p}$$  [Formula 2]

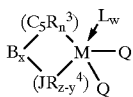

[Formula 3]

where M is a transition metal of Group IVB of the Periodic Table;

($C_5R^3_m$) or ($C_5R^{3'}_n$) is a cyclopentadienyl or substituted cyclopentadienyl, each $R^3$ which can be the same or different, is a hydrogen radical, an alkyl radical, an arylalkyl radical, an alkylaryl radical, an aryl radical, of 1 to 20 carbon atoms, a halogen radical, and an alkoxy radical of 1 to 20 carbon atoms, or a metalloid radical of metal of Group 14 (Ivb in the previous IUPAC form) substituted with hydrocarbyl group, a cyclopentadienyl or substituted cyclopentadienyl ligand in which two adjacent carbon atoms are joined together to form one or more $C_4$–$C_8$ rings by a hydrocarbyl radical;

B is a bridge joining two cyclopentadienyl ligands or a cyclopentadienyl ligand and $JR^4_{z-y}$ by a covalent bond, which is selected from the group of consisting of an alkylene radical of 1 to 4 carbon atoms, a dialkylsilicone radical, a dialkylgermanium radical, an alkyl phosphine radical, or an amine radical $R^4$ is selected from the group of consisting of a hydrogen radical, an alkyl radical, an alkenyl radical, an arylalkyl radical, an alkylaryl radical, an aryl radical, of 1 to 20 carbon atoms;

J is an element of Groups VA or VIA of the Periodic Table;

Q is the same or different halogen radical, an alkyl radical, an alkenyl radical, an arylalkyl radical, an alkylaryl radical, an aryl radical, or alkylidene radical, of 1 to 20 carbon atoms;

L is a Lewis base and w is greater than 0;

s is 0 or 1, p is 0, 1 or 2, when p is 0, s is 0, when s is 1, m is 4, and when s is 0, m is 5;

z is a valence number of J, and is 3 for element of Group VA, and 2 for Group VIA; and x is 0 or 1, when x is 0, n is 5, y is 1, when x is 1, n is 4, y is 2.

The Molecular structure of representative metallocene catalysts which can be used in the present invention is described at Table 1. However, it is not limited to this, as here X is ethoxy or methoxy and n is possibly 1~20.

As has been reported by R. Jackson etc., (R. Jackson, J. Ruddlesden. And D. J. Thompson, R, Whelan, J. Organomet. Chem. 125 (1997). 57; B. L. Booth. G. C. Ofunne. C. Stacey, and P. J. T. Tait, J. Organomet. Chem. 135 (1986), 145; European Patent No. 293815), metallocene catalyst can be synthesized by metallation of the cyclopentadienyl ligands having an alkoxysilane group, but more easily synthesized in hydrosilylation of the metallocene compounds having alkenyl or alkynyl group.

A supporting material having a highly reactive siloxane group on its surface produced by drying at high temperature is used in the present invention. In detail, silica-alumina, silica-magnesia, etc. dried at a high temperature could be used and these generally contain an oxide compound, and a carbonate, a sulfate, and a nitrate consisting of $Na_2O$, $K_2CO_3$, $BaSO_4$, $Mg(NO)_2$, etc. The most major characteristics of the present invention is to use a support having a highly reactive siloxane group on its surface which is dried at high temperatures with flowing air, nitrogen, and inert gas or at reduced pressure, removing water and OH groups on that supporting materials. The preferred drying temperature is over 600° C. The less amount of OH group on the surface, the better. However, it is practically difficult to remove all OH groups. The amount of OH groups is preferably less than 0.5 mmol/g. The amount of surface OH groups can be controlled by the drying temperature, drying time, drying method, etc. In order to reduce the side reaction by some remaining OH groups, a support may be chemically modified to transform OH to other unreactive group such as $OSiMe_3$ group.

Supported catalyst is manufactured by reacting the above described catalyst with a support. As a solvent, most of organic solvents including an aliphatic hydrocarbon solvent; like hexane or pentane, an aromatic hydrocarbon solvent; like toluene or benzene, a chlorine atom substituted hydrocarbon solvent, like dichloromethane, an ether base solvent, like diethylether or tetrahydrofuran, acetone, ethylacetate, etc., can be used. However, hexane, haptan, toluene, and dichloromethane are the most desirable. Reaction without solvents is also possible. Although possible reaction temperatures range from −30° C. to 150° C., The preferable temperature is from room temperature to 100° C. After filtering reacting solvents, removing through reduced distillation, and Soxhlet filtering with toluene if necessary, the reacted supporting catalyst itself could be used.

This manufactured supported catalyst could be used in the olefin polymerization by activation with compounds represented in Formulae 4, 5, or 6 respectively or by using the mixture thereof.

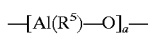 <Formula 4>

Wherein, each $R^5$, which can be the same or different, is selected from a group comprising halogen, hydrocarbyl radicals having from 1 to 20 carbon atoms, or substituted hydrocarbyl radicals having 1 to 20 carbon atoms substituted by a halogen. The subscript a is an integral number over 2, and this compound can exists in a linear, circular, or network structure.

 <Formula 5>

Wherein N is aluminum or boron, $R^5$ is defined the same as in the above described Formula 4, with each three of $R^5$ groups can be the same or different.

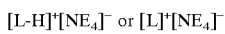 <Formula 6>

Wherein L is a neutral or positive ionic Lewis acid, H is a hydrogen atom, N is an element of Group 13 (IIIb in the previous IUPAC form), e.g., aluminum and boron, each E, which can be the same or different, is an aryl radical having from 6 to 20 carbon atoms, where more than one hydrogen radical were substituted with halogen radical, alkoxy radical, or phenoxy radical.

Examples of compound described in the above Formula 4 include methylaluminoxane, ethylaluminoxane, isobutylaluminoxane, butylaluminoxane, etc. Examples of alkyl metal compounds described in the above Formula 5 include trimethylaluminum, triethylaluminum, triisobutylaluminum, tripropylaluminum, tributylaluminum, dimethylchloroaluminum, triisopropylaluminum, tri-s-butylaluminum, tricyclopentylaluminum, tripentylaluminum, triisopentylaluminum, trihexylaluminum, ethyidimethylaluminum, methyidiethylaluminum, tripentylaluminum, tri-p-tolrylaluminum, dimethylaluminummethoxide, dimethylaluminumethoxide, trimethylboron, triethylboron, triisobutylboron, tripropylboron, tributylboron, etc. Examples of compound in Formula 6 include triethylammoniumtetraphenylboron, tributylammoniumphenylboron, trimethylammoniumtetraphenylboron, tripropylammoniumtetraphenylboron, trimethylammoniumtetra(p-tolyl)boron, trimethylammoniumtetra(o,p-dimethylphenyl)boron, tributylammoniumtetra(p-trifluoromethylphenyl)boron, trimethylammoniumtetra(p-trifluoromethylphenyl)boron, tributylammoniumtetraphentafluorophenylboron, N,N-diethylammilidiumtetraphenylboron, N,N-diethylanilidiumtetraphenylboron, N,N-diethylaniliumtetraphentafluorophenylboron, diethylammoniumtetraphentfluorophenylboron, triphenylphosphoniumtetraphenylboron, trimethylphosphoniumtetraphenylboron, triethylammoniumtetraphenylaluminum, tributylammoniumtetraphenylaluminum, trimethylammoniumtetraphenylaluminum, tripropylammoniumtetraphenylaluminum, trimethylammoniumtetra(p-tolyl)aluminum, triethylammoniumtetra(o,p-dimethylphenyl)aluminum, tributylammoniumtetra(p-tfluoromethylphenyl)aluminum, trimethylammoniumtetra(p-trifluoromethylphenyl) aluminum, tributylammoniumtetrapentafluorophenylaluminum, N,N-diethylanniliumtetraphenylaluminum, N,N-diethylanniliumtetraphenylaluminum, N,N-diethylanniliumtetrapentafluorophenylaluminum, diethylammoniumtetrapentafluorophenylaluminum, triphenylphosphoniumtetraphenylaluminum, trimethylphosphoniumtetraphenylaluminum, triethylammoniumtetraphenylaluminum, tributylammoniumtetraphenyltetraphenylaluminum, trimethylammoniumtetraphenylboron, tripropylammoniumtetraphenylboron, trimethylammoniumtetra(p-tolyl)boron, tripropylammoniumtetra(p-tolyl)boron, triethylammoniumtetra(o,pdimethylphenyl)boron, trimethylammoniumtetra(o,p-dimethylphenyl)boron, tributylammoniumtetra(p-trifluoromethylphenyl)boron, trimethylammoniumtetra(p-trifluoromethylphenyl)boron, tributylammoniumtetrapentafluorophenylboron, N,N-diethylanniliumtetraphenylboron N,N-diethylanniliumtetraphenylboron, N,N-diethylanniliumtetrapentafluorophenylboron, diethylammoniumtetrapentafluorohenylboron, triphenylphsphoniumtetraphenylboron, triphenylcarboniumtetra(p-trifluoromethylphenyl)boron, triphenylcarboniumtetrapentafluorophenylboron, etc.

Solvents used when manufacturing olefin based polymer by using the above described supported catalyst and cocatalyst include aliphatic hydrocarbon solvents, e.g., pentane, hexane, haptan, nonan, decan, and their isomers and aromatic hydrocarbonate solvents, like toluene or benzene, chlorine atom substituted hydrocarbon solvents, like dichloromethane or chlorobenzene, and mixtures of two or more of these solvents.

Examples of olefin based monomer, which is capable of polymerization by using the above described support catalyst and cocatalyst, include ethylene, α-olefin, cyclic olefin, etc., diene monomers having more than two double bonds or triene monomers, etc., are also capable of polymerization.

Examples of the above described monomers include ethylene, propylene, 1-butyl, 1-pentene, 4-methyl-1-pentene, 1-hexane, 1-hapten, 1-decene, 1-undecene, 1-dodecene, 1-tetradecene, 1-hexandecene, 1-icocene, nobonene, nobonadien, ethylidennoboden, vinylnobonene, dicyclopentadien, 1,4-butadien, 1,5-pentadien, 1,6-hexadien, styrene, α-methylstyrene, divinylbenzene, 3-chloromethylstyrene, etc. Copolymerization could be done by mixing more than one of these monomers.

Polymerization is performed at temperature ranging from 25° C. to 500° C. and the pressures ranging from 40 psi to 800 psi. It is preferable to add catalyst in an amount that is 1 to 30,000 times the metallocene mole content. In the present invention, contact order and input order of catalyst, cocatalyst, solvent, and monomer are not particularly restricted. That is, polymerization is done by putting the above described support catalyst and cocatalyst into suspension solvents simultaneously, or main polymerization could be done after either the activation reaction or prepolymerization. Prepolymerized cataylst can be obtained by filtering or decanting after stirring of supported catalyst activated with cocatalyst in the presence of olefin under the appropriate temperature and pressure. Activated catalysts can be obtained as the same method of prepolymerization reaction without olefin.

Although the present invention is illustrated by the following practical exercises in detail, the range of the present invention is not limited by these practical exercises.

EXAMPLE 1

Organic reagents and solvents, which are needed in catalyst manufacturing and polymerization, were bought from Aldrich and Merck, refined by standard methods. Ethylene was polymerized after passing high purified products bought from Applied Gas Technology through moisture and oxygen filtering equipment, test reproductability was increased by blocking contact between air and moisture at all stages of catalyst synthesizing, injecting and polymerizing. Molecular weight of the polymerized polymer was measured by is high temperature Gel Permeation Chromatography. It was measured after making universal correction curves of polystyrene standard samples and dissolving polymerized polymer by using Waters' model 150 V attaching a concentration detector capable of measuring refraction ratio and viscosity simultaneously. After dissolving into $CDCl_3$ solvents a spectrum was obtained by using a 270 MHz Joel Nuclear Magnetic Resonator(NMR) or a 300 MHz Bruker NMR in order to identify the structure of catalysts. The supporting amount of support catalyst was found by measuring the Zr amount with the Inductively Coupled Plazma(ICP) spectroscopic method. The amount of surface silica hydroxyl group was obtained by titrating with MeMgl, following the method J. J. Fripiat and J. Uytterhoeven published in Journal of Physical Chemistry, 66, 800 (1962).

a) Synthesizing of Catalysts Having an Alkoxysilane Group:
  1) Synthesizing of $[CH_2=CH(CH_2)_4C_5H_4]_2ZrCl_2$ 9-hexene-1-all 10.36 g, paratoluenesulfonylchloride 24.11 g and diethylether 200 ml was put into one opening flask and mixed well. Well grounded high temperature powder of potassium hydroxide 353.5 g was slowly added at temperature for about 10 minutes after decreasing the temperature of the flask to −10° C. by dipping it into the low temperature vat. It was then agitated at −15° C. to −5° C. for about 30 minutes. After that, this solution was poured into 200 ml of cold iced water. After collecting esther layers by fractional funnelling and removed moisture by inserting anhydrous magnesium sulfate, magnesium sulfate was removed by filtering to obtain a colorless viscous compound solution a 200 ml shrank flask. Ether was removed with reduced a pressure rotational distiller. Anhydrous THF (Tetrahydrofuran) 120 ml was then poured into a Schlenk flask containing this compound. After this, the flask was dipped into an iced low temperature vat, and NaCp (2 M, tetrahydrofuran) 62 ml was injected into the flask. It was then agitated at the room temperature for about 3 to 5 hours after removing the iced low temperature vat. Organic layers were mixed and collected after pouring this solution into a 1 liter fractional funnel, filled with 200 ml of water and 200 ml of hexane. Magnesium sulfate was removed by removing moisture and filtering after putting anhydrous magnesium sulfate into the organic layers. All solvents were removed with a reduced pressure distiller. A somewhat yellow liquid compound was obtained and 9.643 g of hexenylcyclopentadien compound was obtained by vacuum distillation (yield: 65%).

The above manufactured 9.643 g of decenylcyclopentadien and 100 ml of THF (tetrahydrofuran) were put into a 250 ink, Schlenk flask. After decreasing temperature of this to −78° C. with a aceton-dryice low temperature vat, 26 ml of n-butyllitium (2.5 M, hexane solution) was slowly supported during agitation. The temperature was increased to room temperature and it was agitated overnight at a room temperature. After weighing in the dry box, 12.26 g $ZrCl_4$ $(THF)_2$ was made from $ZrCl_4$ compound according to the method described in Inorganic Synthesis 1982, vol. 21, 135, by putting it into a 500 ml Schlenk flask with, 200 ml of anhydrous toluene. Then THF (tetrahydrofuran) solution, which has been agitated all night, and toluene solution were mixed, where $ZrCl_4$ $(THF)_2$ was contained without air contact at a room temperature. This mixture was agitated at 50 to 60° C. for 3 days. Solvents were removed by vacuum after lowering the temperature to 40° C. 20 ml of hexane were heated somewhat to melting formed solid material and then filtered while in the heated state without air contact. Hexane again was removed from the filtered solution by vacuum pump and the desired white solid compound was obtained. The yield was 65%.

$H_1$ Nuclear Magnetic Resonator analysis (300 MHz, CDCl3): 6.27 (2 H. t, J=2.6 Hz), 6.18 (2 H, t. J=2.6 Hz), 5.77(1 H, ddt, J=7.5 Hz), 2.1–2.0(2 H, t, J=7.5 Hz), 2.1–2. (2 H, m), 1.6–1.3(4 H, m); $^{13}C$ Nuclear Magnetic Resonator analysis (CDCl$_3$) 138.6, 134.9, 116.7, 114.5, 112.2, 33.4, 30.1, 30.0, 28.5.

2) Synthesizing of $[Cl(Me)_2Si—(CH_2)_6C_5H_4]_2ZrCl_2$

After weighing in the dry box the above 1.28 g of synthesized $[CH_2=CH(CH_2)_4C_5H_4]_2ZrCl_2$ was put it into 100 ml Shrank flask. After taking it out of the dry box, 5 ml of toluene 5 ml and 1.2 ml of chlorodimetalsilane are added while agitating. It was then gitated at a room temperature for one day after putting 20 ml of $H_2PtCl_6$ isopropanol solution (0.1 M). All solvents were removed with a vacuum pump, and it was then heated somewhat with 100 ml. of hexane to melt solids that have formed. It was filtered in the hot state, the filtered solution put in the refrigerator, and left alone for one day, obtaining a white crystal (yield: 90%).

$^1H$ Nuclear Magnetic Resonator analysis (500 MHz, CDCl$_3$): 6.27 (2 H, t. J=2.4 Hz), 6.18 (2 H, t. J=2.4 Hz), 2.60 (2 H, t. J=7.5 Hz) 1.7–1.45 (2 H. m), 1.45–1.1 (4 H, m), 0.85–0.75 (2 H, m), 0.37 (6 H, s); $^{13}C$ Nuclear Magnetic Resonator Analysis (CDCl$_3$): 134.9, 116.6, 112.2, 32.5, 30.3, 30.0, 22.8, 18.8, 1.6.

3) Synthesizing of $[(EtO)(Me)_2Si—(CH_2)_6C_5H_4]_2ZrCl_2$

After putting 4.7 ml of trimethylorthoformate into the above manufactured 1.63 g of $[Cl(Me)_2Si—(CH_2)_6C_5H_4]_2ZrCl_2$ compound, the mixture was agitated well and about 1 mg of anhydrous $AlCl_3$ was added and the reaction progress with gas appearing. About two hours later, gassing stopped. After the removal of all volatile materials, 30 ml of hexane was added and dissolved it. After filtering and removing all solvents with a vacuum pump, an oily solid compound (yield 1.60 g, 95%) was obtained.

$^1H$ Nuclear Magnetic Resonator Analysis (300 MHz, CDCl$_3$): 6.27 (2H. t, J=2.7 Hz), (2H, t. J=2.7 Hz), 3.62 (2 H, q, J=7.2 Hz), 2.60 (2 H, t. J=7.5 Hz) 1.7–1.2(16 H. m). 1.16 (3 H, t, J=7.2 Hz), 0.65–0.45 (2 H, m) 0.06 (6 H, s); $^{13}C$ Nuclear Magnetic Resonator Analysis (CDCl$_3$) 135.1, 116.6, 112.3, 58.1, 33.1, 30.2, 30.2, 29.0, 23.1, 18.5, 16.3, 0.37.

b) Drying of Silica

After weighting, 2.0 g of Grace Davison 948 silica was put into a crystal container, and placed into a furnace manufactured by Lindberg, where the temperature was increased at the rate of 7° C./min reaching 800° C. and then cooled from this temperature over 21 hours. Using the same method, silica was dried at 200° C., 400° C. and 600° C.

c) Drying of Support Catalyst

The silica dried at b) above was moved from the dry box to a Schlenk flask and sealed, in order to be taken out. A solution (concentration: 37 mg/ml) in which catalyst, $[(EtO)(Me)_2Si—(CH_2)_6C_5H_4]_2ZrCl_2$, was dissolved in hexane was made and 3.6 ml of this solution (2.0 mmol) 30 ml of hexane were mixed. This slurry was refluxed for 18 hours. Hexane was removed by distilling at a vacuum, this support catalyst was extracted for two days by using a Soxhlet's extractor and using toluene as a solvent. All catalysts which were not supported by the characteristic bond were removed. The amount of support catalyst according to the drying temperature is represented in Table 1.

d) Polymerization

After weighing 100 mg of support catalyst manufactured at c) in the dry box, it was put into a glass reactor, sealed in the reactor and taken out of the dry box. 200 ml of refined hexane were put into this reactor and placed in 2.0 ml of aluminoxane MMAO-3 (6. % Al) melted in haptan manufactured by Akzo. After agitating at 80° C. for 5 minutes, ethylene was poured in under the pressure of 40 psig. This was polymerized for one hour at this temperature and pressure. The reaction was finished by putting 5 ml of ethanol into the reactor. Polymer was obtained after filtering and drying in an 80° C. oven. The polymer amount, activity, polymer molecular weight, and molecular weight distribution according to the drying temperature of silica are represented in Table 1.

Table 1 shows the relation between drying temperature and amount of hydroxyl group, support amount of catalyst obtained at this time, activity, molecular weight of polymer obtained by this supported catalyst, and molecular weight distribution.

TABLE 1

| Drying temperature (° C.) | OH amount mmol/g | Supported amount Zr % (based on total weight of supported catalyst) | Polymer amount g | Activity KgPE/Zr h | Molecular weight Mw | Molecular weight distribution Mw/Mn |
|---|---|---|---|---|---|---|
| 200 | 11.8 | 1.1 | 6.7 | 0.56 | 324500 | 3.37 |
| 400 | 0.85 | 1.1 | 8.7 | 0.73 | 328000 | 0.63 |
| 600 | 0.54 | 0.98 | 13.6 | 1.2 | 192000 | 2.79 |
| 800 | 0.35 | 0.85 | 13.7 | 1.5 | 189000 | 2.64 |

It is shown that as expected the higher the drying temperature is, the less the amount of hydroxyl groups. Although the deposit amount is also somewhat decreased as the amount of surface hydroxyl groups decreases, there is not much affect because catalyst can be deposited by the reaction with a hydroxyl group, and deposit is also possible by the reaction with high reactive siloxane group. As it is noted in FIG. 1, the fact that the less the amount of hydroxyl group becomes, the more the amount of monomer obtained and the more metal activities increase means the deposited catalyst reacted by reacting with hydroxyl groups as expected with large non-active areas due to side reactions, and on the contrary, deposited catalyst by siloxane groups shows most of activities due to less side reactions. The fact that the less hydroxyl group the more narrow molecular weight distribution, an inherent characteristic of metallocene catalyst, means deposited catalyst by siloxane groups is attached as a desired form, and deposited catalyst by hydroxyl groups change into various forms of catalysts by side reactions. That is, Table 1 and FIG. 1 show there is more advantages in activity and molecular weight distribution when depositing metallocene catalyst having an alkoxysilane group, an important characteristic of the present invention, having small hydroxyl groups and high reactive siloxane groups than when using the existing hydroxyl groups. Particularly, it is noted that when the amount of hydroxyl group is lower than 0.5 mmol/g, which is limited in European Patent No. 293815, metal activities are maximized and Mw/Mn shows minimum values.

While the present invention has been described in detail with reference to the preferred embodiments, those skilled in the art will appreciate that various modifications and substitutions can be made thereto without departing from the spirit and scope of the present invention as set forth in the appended claims.

What is claimed is:

1. A supported metallocene composition, comprising a support composition and a metallocene moiety bonded to the support composition, wherein the support composition comprises less than 0.5 mmol/g hydroxyl groups per gram of support composition, wherein the support composition comprises a single oxygen siloxane connection, in which two silicons are bonded with one intervening oxygen as shown below:

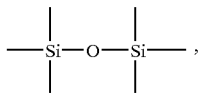

wherein the metallocene moiety is bonded to one of the silicon in the single oxygen siloxane connection, wherein a hydrocarboxy group is bonded to the other silicon in the single oxygen siloxane connection, and wherein the hydrocarboxy group is selected from the group consisting of alkoxy, arylalkoxy, alkylaroxy and aroxy.

2. The metallocene composition of claim 1, wherein the metallocene moiety comprises a chemical structure of Formula 2 or Formula 3:

$$(C_5R^3{}_m)_p B_s (C_5R^3{}_M) M Q_{3-p} \quad \text{[Formula 2]}$$

[Formula 3]

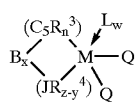

where M is a transition metal;

$(C_5R^3{}_m)$ and $(C_5R^3{}_n)$ are substituted or non-substituted cyclopentadienyl ligands, wherein $R^3$ is a hydrogen radical, a halogen radical, an organic radical or a metalloid radical, wherein when more than one $R^3$'s exist in the metallocene moiety, the $R^3$'s can be either same or different;

B is selected from the group consisting of an alkylene radical of 1 to 4 carbon atoms, a dialkylsilicone radical, a dialkylgermanium radical, an alkyl phosphine radical, and an amine radical;

$R^4$ is a hydrogen radical or an organic radical;

J is an element of Groups VA or VIA of the Periodic Table;

Q is a halogen radical or an organic radical, wherein more than one Q exist in the metallocene moiety, the Q's can be either same or different;

L is a Lewis base;

w is greater than 0;

p is 0, 1 or 2;

s is 0 or 1, wherein when p is 0, s is 0, wherein when s is 1, m is 4, and wherein when s is 0, m is 5;

z is a valence number of J, wherein z is 3 for element of Group VA, and wherein z is 2 for Group VIA; and x is 0 or 1, wherein when x is 0, n is 5, and y is 1, and wherein when x is 1, n is 4, y is 2.

3. The metallocene composition of claim 2, wherein the organic radical for $R^3$ is of 1 to 20 carbon atoms and selected from the group consisting of an alky radical, an arylalkyl radical, an alkylaryl radical, an aryl radical, and an alkoxy radical, and wherein the metalloid radical for $R^3$ is of metal of Group 14 (Ivb in the previous IUPAC form) substituted with a hydrocarbon group, a non-substituted cyclopentadienyl or substituted cyclopentadienyl ligand in which two adjacent carbon atoms are joined together to form one or more $C_4$–$C_8$ rings by a hydrocarbon radical.

4. A method of preparing a supported metallocene composition, the method comprising:

providing a support composition, the support composition comprising less than 0.5 mmol/g hydroxyl groups per gram of support composition, the support composition further comprising a double oxygen siloxane connection, in which two silicons are bonded with two intervening oxygens as shown below:

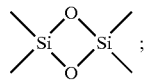

providing a metallocene compound comprising a metallocene moiety and an alkoxysilane group;

reacting the double oxygen siloxane connection of the support composition with the alkoxysilane group of the metallocene compound so as to produce a supported metallocene composition comprising a single oxygen siloxane connection, in which two silicons are bonded with one intervening oxygen as shown below:

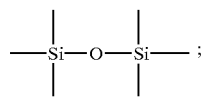

wherein the metallocene moiety is bonded to one of the silicon in the single oxygen siloxane connection, wherein a hydrocarboxy group is bonded to the other silicon in the single oxygen siloxane connection, and wherein the hydrocarboxy group is selected from the group consisting of alkoxy, arylalkoxy, alkylaroxy and aroxy.

5. The method of claim 4, wherein the provision of the support composition comprising a double oxygen siloxane connection comprises:

providing a support composition comprising a single oxygen siloxane connection, in which two silicons are bonded with one intervening oxygen as shown below:

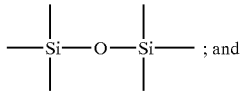 ; and changing the single oxygen siloxane connection to the double oxygen siloxane connection.

6. The method of claim 4, wherein the metallocene moiety comprises a chemical structure of Formula 2 or Formula 3:

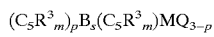 [Formula 2]

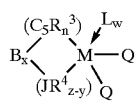 [Formula 3]

where M is a transition metal;

$(C_5R^3_m)$ and $(C_5R^3_n)$ are substituted or non-substituted cyclopentadienyl ligands, wherein $R^3$ is a hydrogen radical, a halogen radical, an organic radical or a metalloid radical, wherein when more than one $R^3$'s exist in the metallocene moiety, the $R^3$'s can be either same or different;

B is selected from the group consisting of an alkylene radical of 1 to 4 carbon atoms, a dialkylsilicone radical, a dialkylgermanium radical, an alkyl phosphine radical, and an amine radical;

$R^4$ is a hydrogen radical or an organic radical;

J is an element of Groups VA or VIA of the Periodic Table;

Q is a halogen radical or an organic radical, wherein more than one Q exist in the metallocene moiety, the Q's can be either same or different;

L is a Lewis base;

w is greater than 0;

p is 0, 1 or 2;

s is 0 or 1, wherein when p is 0, s is 0, wherein when s is 1, m is 4, and wherein when s is 0, m is 5;

z is a valence number of J, wherein z is 3 for element of Group VA, and wherein z is 2 for Group VIA; and x is 0 or 1, wherein when x is 0, n is 5, and y is 1, and wherein when x is 1, n is 4, y is 2.

7. The method of claim 6, wherein the organic radical for $R^3$ is of 1 to 20 carbon atoms and selected from the group consisting of an alky radical, an arylalkyl radical, an alkylaryl radical, an aryl radical, and an alkoxy radical, and wherein the metalloid radical for $R^3$ is of metal of Group 14 (Ivb in the previous IUPAC form) substituted with a hydrocarbon group, a non-substituted cyclopentadienyl or substituted cyclopentadienyl ligand in which two adjacent carbon atoms are joined together to form one or more $C_4$–$C_8$ rings by a hydrocarbon radical.

8. The method of claim 6, wherein in Formula 2, B covalent-bonds the two cyclopentadienyl ligands, and wherein in Formula 3, B covalent-bonds the cyclopentadienyl ligand and $JR^4_{z-y}$.

9. The method of claim 6, wherein the organic radical for $R^4$ is of 1 to 20 carbon atoms and selected from the group consisting of an alkyl radical, an alkenyl radical, an arylalkyl radical, an alkylaryl radical, and an aryl radical.

10. The method of claim 6, wherein the organic radical for Q is of 1 to 20 carbon atoms and selected from the group consisting of an alkyl radical, an alkenyl radical, an arylalkyl radical, an alkylaryl radical, an aryl radical, and alkylidene radical.

11. The method of claim 4, wherein the provision of the metallocene compound comprises substituting a hydrogen radical in $R^3$, $R^4$ and B of a compound of either Formula 2 or Formula 3 with at least one radical of Formula 1 as appearing below:

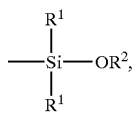 [Formula 1]

wherein $R^1$ is a hydrogen radical, a halogen radical, or an organic radical, and wherein $R^2$ is an organic radical.

12. A method of polymerizing an olefin, comprising:

providing a supported metallocene composition, which comprises a support composition and a metallocene moiety bonded to the support composition, wherein the support composition comprises less than 0.5 mmol/g hydroxyl groups per gram of support composition, wherein the support composition comprises a single oxygen siloxane connection, in which two silicons are bonded with one intervening oxygen as shown below:

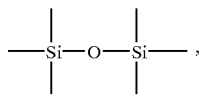

wherein the metallocene moiety is bonded to one of the silicon in the single oxygen siloxane connection, wherein a hydrocarboxy group is bonded to the other silicon in the single oxygen siloxane connection, and wherein the hydrocarboxy group is selected from the group consisting of alkoxy, arylalkoxy, alkylaroxy and aroxy; and polymerizing an olefinic monomer in the presence of the supported metallocene composition.

13. The method of claim 12, wherein the polymerization is carried out in the further presence of a cocatalyst.

14. The method of claim 12, wherein the cocatalyst comprises a compound of Formula 4, Formula 5, Formula 6, or Formula 7 as appearing below:

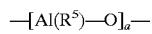 [Formula 4]

 [Formula 5]

wherein $R^5$ is a halogen radical or a hydrocarbon radical, wherein the $R^5$'s can be either same or different, and wherein a is an integral number greater than 2;

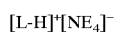 [Formula 6]

 [Formula 7]

wherein L is a neutral or a positive ionic Lewis base, wherein H is a hydrogen atom, wherein N is an element of Group 13 (IIIb in the previous IUPAC form), wherein E is an aryl radical, and wherein E's can be either same or different.

* * * * *